United States Patent
Kohiyama et al.

(10) Patent No.: US 11,371,987 B2
(45) Date of Patent: Jun. 28, 2022

(54) METHOD OF AMPLIFYING DETECTION LIGHT USING LIGHT-REFLECTING MATERIAL, IN IMMUNOCHROMATOGRAPHY

(71) Applicant: Denka Company Limited, Tokyo (JP)

(72) Inventors: Risa Kohiyama, Gosen (JP); Osamu Ishikawa, Gosen (JP); Takashi Miyazawa, Gosen (JP)

(73) Assignee: Denka Company Limited, Tokyo (JP)

(*) Notice: Subject to any disclaimer, the term of this patent is extended or adjusted under 35 U.S.C. 154(b) by 381 days.

(21) Appl. No.: 16/420,594

(22) Filed: May 23, 2019

(65) Prior Publication Data

US 2019/0277838 A1   Sep. 12, 2019

Related U.S. Application Data

(62) Division of application No. 14/909,306, filed as application No. PCT/JP2014/070206 on Jul. 31, 2014, now Pat. No. 10,345,294.

(30) Foreign Application Priority Data

Aug. 2, 2013  (JP) .............................. JP2013-161691

(51) Int. Cl.
| | | |
|---|---|---|
| *G01N 33/543* | (2006.01) | |
| *G01N 33/558* | (2006.01) | |
| *B01D 15/38* | (2006.01) | |
| *G01N 21/64* | (2006.01) | |
| *G01N 33/545* | (2006.01) | |

(52) U.S. Cl.
CPC ... *G01N 33/54313* (2013.01); *B01D 15/3809* (2013.01); *G01N 21/6428* (2013.01); *G01N 33/545* (2013.01); *G01N 33/54386* (2013.01); *G01N 33/558* (2013.01); *G01N 33/54388* (2021.08); *G01N 2021/6439* (2013.01); *G01N 2201/0636* (2013.01)

(58) Field of Classification Search
None
See application file for complete search history.

(56) References Cited

U.S. PATENT DOCUMENTS

| | | |
|---|---|---|
| 4,363,874 A | 12/1982 | Greenquist |
| 6,194,224 B1 | 2/2001 | Good et al. |
| 2002/0045195 A1* | 4/2002 | Hubscher ............ G01N 33/558 435/7.9 |
| 2003/0104486 A1 | 6/2003 | Selvan |
| 2005/0037510 A1 | 2/2005 | Sharrock et al. |
| 2005/0109951 A1 | 5/2005 | Fish et al. |
| 2007/0292897 A1 | 12/2007 | Yazawa et al. |
| 2008/0153125 A1 | 6/2008 | Buttry et al. |
| 2013/0164734 A1 | 6/2013 | Raychaudhuri et al. |

FOREIGN PATENT DOCUMENTS

| | | |
|---|---|---|
| EP | 0291194 A1 | 11/1988 |
| EP | 1484611 A2 | 12/2004 |
| JP | 06-055084 A | 3/1994 |
| JP | 2004-361410 A | 12/2004 |
| JP | 2005-515429 A | 5/2005 |
| JP | 2007-333695 A | 12/2007 |
| JP | 2012-032263 A | 2/2012 |
| JP | 2013-002851 A | 1/2013 |
| WO | WO 2009/144507 A1 | 12/2009 |
| WO | WO 2011/014673 A1 | 2/2011 |

OTHER PUBLICATIONS

MacLeod. "Thin film optical filters", A. Hilger, London, (1985), p. 137-138 (4 pages total attached) (Year: 1985).*
International Search Report dated Nov. 11, 2014, in PCT/JP2014/070206, (2 pages).
Supplementary European Search Report dated Feb. 16, 2017, in EP 14831189.7, (10 pages).

* cited by examiner

*Primary Examiner* — Ellen J Marcsisin
(74) *Attorney, Agent, or Firm* — Foley & Lardner LLP

(57) ABSTRACT

The present invention intends to provide an immunochromatographic test piece that makes it possible to achieve both highly sensitive detection of a substance to be detected and a simple test piece structure, which are usually difficult to be made compatible with each other. The immunochromatographic test piece is an immunochromatographic test piece comprising a membrane on which a capture substance being a ligand that bonds to a substance to be detected is immobilized, wherein insoluble carrier particles to which a ligand that bonds to the substance to be detected is bound are used and accumulated by being captured with the capture substance immobilized on the membrane, the membrane is irradiated with light to detect light emitted from a portion where the insoluble carrier particles are accumulated or light emitted from a portion surrounding and other than the portion where the insoluble carrier particles are accumulated, thereby measuring the substance to be detected, and a light-reflecting material is provided on a side of the membrane opposite to a side irradiated with light.

6 Claims, 10 Drawing Sheets

⊢—⊣ Portion where insoluble carrier particles are accumulated

A. MacLeod "Thin film optical filters", A. Hilger, London, 1985

Sectional view

Sectional view

Sectional view

Sectional view

Sectional view

METHOD OF AMPLIFYING DETECTION LIGHT USING LIGHT-REFLECTING MATERIAL, IN IMMUNOCHROMATOGRAPHY

CROSS-REFERENCE TO RELATED APPLICATIONS

This application is a Divisional of U.S. application Ser. No. 14/909,306, which is the U.S. National Stage of PCT/JP2014/070206, filed Jul. 31, 2014, which claims priority from Japanese application JP 2013-161691, filed Aug. 2, 2013.

TECHNICAL FIELD

The present invention relates to a method for specifically and rapidly detecting a substance to be detected in a specimen, and to a kit using the same.

BACKGROUND ART

Immunochromatography is an immunological method for analyzing the presence or absence of a substance to be detected, in which method insoluble carrier particles to which a ligand that specifically recognizes the substance to be detected is bound are used, the insoluble carrier particles capture the substance to be detected, move in a test piece with a fiber structure making use of a capillary phenomenon, and bond to a capture substance that specifically bonds to the substance to be detected immobilized at a predetermined position in the test piece resulting in accumulation of aggregated insoluble carrier particles at a predetermined position in the test piece, and the accumulation of the aggregated insoluble carrier particles are utilized to detect the presence or absence of the accumulation of the insoluble carrier particles by visual observation or with a detection apparatus. The immunochromatography is widely used, due to its simplicity, for pharmaceutical products for in vivo diagnosis of POCT (Point of Care Test) not for laboratory.

Conventionally, as particles that are objects to label a ligand that specifically recognizes a substance to be detected, insoluble carrier particles such as gold colloid, platinum-gold colloid, and colored polystyrene particles have been used, and the presence or absence of the accumulation of the particles has been determined making use of the hue of various particles by visual observation or with a dedicated apparatus.

Further, improving the sensitivity by using fine particles that emit fluorescence while making the most of the simplicity attributable to immunological aggregation reaction is proposed (see Patent Literature 1) for achieving high sensitivity as a problem.

Moreover, when the fine particles that emit fluorescence are used, an apparatus dedicated to highly sensitive detection of the particles is essential. The portability of the apparatus is an extremely important problem when utilization as a POCT is taken into consideration.

In order to solve the problem, an apparatus for detecting fluorescence which is extremely portable, which is inexpensive and robust, and which has a high sensitivity is proposed (see Patent Literature 2).

Even though proposals for a highly sensitive detection method using such particles that emit fluorescence or such an apparatus in immunochromatography have been made, a technology has not been proposed yet that enables highly sensitive detection by improving a test piece and a case that stores the test piece, not improving particles, in a test system where particles that are accumulated at a predetermined position on the test piece and that emit fluorescence are irradiated with light and light emitted from the excited particles is detected.

CITATION LIST

Patent Literature

Patent Literature 1: Japanese Patent Publication (Kokai) No. 2012-32263
Patent Literature 2: Japanese Patent Publication (Kohyo) No. 2005-515429

SUMMARY OF INVENTION

Technical Problem

In achieving high sensitivity with a dedicated detection apparatus, the mechanism of detection in the detection apparatus has to be much complicated, and on the other hand, it is essential to dispose of a test piece (POCT kit main body) after use to which a test has been conducted using an organism-derived substance that contains a substance to be detected. In order to spread the test piece at clinical sites and adapt the test piece to various fields, handling of the test piece is required to be simple and the test piece is required to be inexpensive. In order to achieve these, the structure of the test piece has to be simple.

The present invention intends to provide an immunochromatographic test piece that makes it possible to achieve both highly sensitive detection of a substance to be detected and a simple test piece structure, which are usually difficult to be made compatible with each other.

Solution to Problem

In the measurement using a detection apparatus such as a fluorescence detection apparatus, a test piece is irradiated with excitation light having a constant wavelength from a light source included in the detection apparatus. Particles which are accumulated on the test piece and emit fluorescence receive the excitation light to emit fluorescence having a particular wavelength. The light of a particular wavelength emitted from particles that emit fluorescence is detected with the detection apparatus.

The portion on the test piece where the particles that emit fluorescence are accumulated is irradiated with the excitation light from the detection apparatus, however the particles are not irradiated with the whole excitation light, and much of the light penetrates into the portion under the test piece and is not involved in the generation of fluorescence resulting in the reduction of fluorescence.

The test piece according to the present invention reflects the irradiation light that penetrates into the portion under the test piece by providing a light-reflecting material that reflects the irradiation light at the lower portion of the test piece, so that the accumulated particles that emit fluorescence is efficiently irradiated with the irradiation light to amplify fluorescence to be generated, namely amplify the light to be finally detected. The test piece according to the present invention is not so much different from conventional test pieces, and has a simple structure, not a complicated structure, however the test piece according to the present invention has made it possible to detect a substance to be detected with high sensitivity by providing the reflecting material therein.

Moreover, also when particles colored in a visible range are used instead of the particles that emit fluorescence, by providing the light-reflecting material that reflects the irradiation light at the portion under the test piece, reflected light of irradiation light is attenuated at the portion where particles are accumulated, due to the presence of the particles, and, on the other hand, the intensity of light to be reflected and detected at a portion surrounding and other than the portion where the particles are accumulated is amplified to amplify light to be finally detected, thereby making it possible to detect a substance to be detected with high sensitivity.

That is to say, the present invention is as follows.

[1] An immunochromatographic test piece, comprising a membrane on which a capture substance being a ligand that bonds to a substance to be detected is immobilized, wherein insoluble carrier particles to which a ligand that bonds to the substance to be detected is bound are used and accumulated by being captured with the capture substance immobilized on the membrane; the membrane is irradiated with light to detect light emitted at a portion where the insoluble carrier particles are accumulated or a portion surrounding and other than the portion where the insoluble carrier particles are accumulated, thereby measuring the substance to be detected; and a light-reflecting material is provided on a side of the membrane opposite to a side irradiated with light.

[2] The immunochromatographic test piece according to [1], wherein the insoluble carrier particles are fluorescent labeled insoluble carrier particles, and the membrane is irradiated with excitation light as irradiation light to detect fluorescence emitted from a portion where the insoluble carrier particles are accumulated, thereby measuring the substance to be detected.

[3] The immunochromatographic test piece according to [1], wherein the insoluble carrier particles are colored insoluble carrier particles, and the membrane is irradiated with irradiation light to detect reflected light reflected at the portion where the insoluble carrier particles are accumulated and the portion surrounding and other than the portion where the insoluble carrier particles are accumulated, thereby measuring the substance to be detected.

[4] The immunochromatographic test piece according to any one of [1] to [3], wherein the light-reflecting material having a total reflectance of the irradiation light of 85% or more is used.

[5] The immunochromatographic test piece according to any one of [1] to [4], further comprising a sample addition portion, an absorption band, and a labeled portion.

[6] The immunochromatographic test piece according to any one of [1] to [5], wherein the light-reflecting material is a reflecting material made of a metal.

[7] The immunochromatographic test piece according to [6], wherein the metal is aluminum or copper.

[8] The immunochromatographic test piece according to [7], wherein the irradiation light from 250 nm to 1000 nm is used when the metal is aluminum, and the irradiation light from 600 nm to 1000 nm is used when the metal is copper.

[9] The immunochromatographic test piece according to any one of [1] to [8], wherein the light-reflecting material is provided on the side of the membrane opposite to the side irradiated with the irradiation light so as to make contact with the membrane.

[10] The immunochromatographic test piece according to any one of [1] to [9], stored in a storage container, wherein a light-reflecting material is provided on an inner surface of the storage container, the inner surface being on the side of the membrane opposite to the side irradiated with the irradiation light.

[11] The immunochromatographic test piece according to [10], wherein the light-reflecting material has a structure that collects the reflected irradiation light near the detection portion of the immunochromatographic test piece.

[12] The immunochromatographic test piece according to [10] or [11], wherein the storage container itself is made of the light-reflecting material.

[13] The immunochromatographic test piece according to any one of [1] to [12], wherein the substance to be detected and the ligand that bonds to the substance to be detected are an antigen and an antibody respectively, or an antibody and an antigen respectively.

[14] A method for amplifying detection light in immunochromatography that comprises a membrane on which a capture substance being a ligand that bonds to a substance to be detected is immobilized wherein insoluble carrier particles to which a ligand that bonds to the substance to be detected is bound are used and accumulated by being captured by the capture substance immobilized on the membrane; and the membrane is irradiated with light to detect light emitted at a portion where the insoluble carrier particles are accumulated or a portion surrounding and other than the portion where the insoluble carrier particles are accumulated, thereby measuring the substance to be detected, wherein a light-reflecting material is provided on a side of the membrane opposite to a side irradiated with light.

[15] The method for amplifying detection light according to [14], wherein the insoluble carrier particles are fluorescent labeled insoluble carrier particles, and the membrane is irradiated with excitation light as irradiation light to detect fluorescence emitted from the portion where the insoluble carrier particles are accumulated, thereby measuring the substance to be detected.

[16] The method for amplifying detection light according to [14], wherein the insoluble carrier particles are colored insoluble carrier particles, and the membrane is irradiated with irradiation light to detect reflected light reflected at the portion where the insoluble carrier particles are accumulated and the portion surrounding and other than the portion where the insoluble carrier particles are accumulated, thereby measuring the substance to be detected.

[17] The method for amplifying detection light according to any one of [14] to [16], wherein the light-reflecting material having a total reflectance of the irradiation light of 85% or more is used.

[18] The method for amplifying detection light according to any one of [14] to [17], wherein the light reflecting material is a reflecting material made of a metal.

[19] The method for amplifying detection light according to [18], wherein the metal is aluminum or copper.

[20] The method for amplifying detection light according to [19], wherein the irradiation light from 250 nm to 1000 nm is used when the metal is aluminum, and the irradiation light from 600 nm to 1000 nm is used when the metal is copper.

[21] The method for amplifying detection light according to any one of [14] to [20], wherein the substance to be detected and the ligand that bonds to the substance to be detected are an antigen and an antibody respectively, or an antibody and an antigen respectively.

The present Description includes the contents described in the Description and/or Drawings of Japanese Patent Application No. 2013-161691 on which a priority claim of the present application is based.

Advantageous Effects of Invention

In an immunochromatographic test in which fluorescent dye-labeled insoluble carrier particles or colored insoluble carrier particles are used, and the particles are accumulated on an immunochromatographic test piece to detect fluorescence emitted from the particles, or colored insoluble carrier particles are used, and the particles are accumulated on an immunochromatographic test piece to detect reflected light at a portion where the particles are accumulated and a portion including a portion surrounding and other than the portion where the particles are accumulated, a light-reflecting material is provided on the underside of the portion where insoluble carrier particles are accumulated on the immunochromatographic test piece in the present invention. Thus, when the fluorescent dye-labeled insoluble carrier particles are used, even in the case where excitation light with which the portion where the fluorescent dye-labeled insoluble carrier particles are accumulated is irradiated is transmitted through the membrane, the excitation light is reflected at the light-reflecting material to reach the fluorescent dyes, thereby making it possible to excite the fluorescent dyes. Moreover, part of the generated fluorescence is reflected at the light-reflecting material to be detected as detection light. As a result thereof, the intensity of the detection light that is fluorescence is amplified. Moreover, when the colored insoluble carrier particles are used, the irradiation light is absorbed by the insoluble carrier particles and therefore the reflected light of irradiation light is attenuated due to the insoluble carrier particles, and, on the other hand, the irradiation light is reflected at the portion surrounding and other than the portion where the insoluble carrier particles are accumulated, and the reflected light is detected as amplified detection light. As a result thereof, the sensitivity of detecting a substance to be detected can be made high.

BRIEF DESCRIPTION OF DRAWINGS

FIG. 1A shows a case where fluorescent labeled insoluble carrier particles are used, and FIG. 1B shows a case where colored insoluble carrier particles are used.

DESCRIPTION OF EMBODIMENTS

Figure 1A:
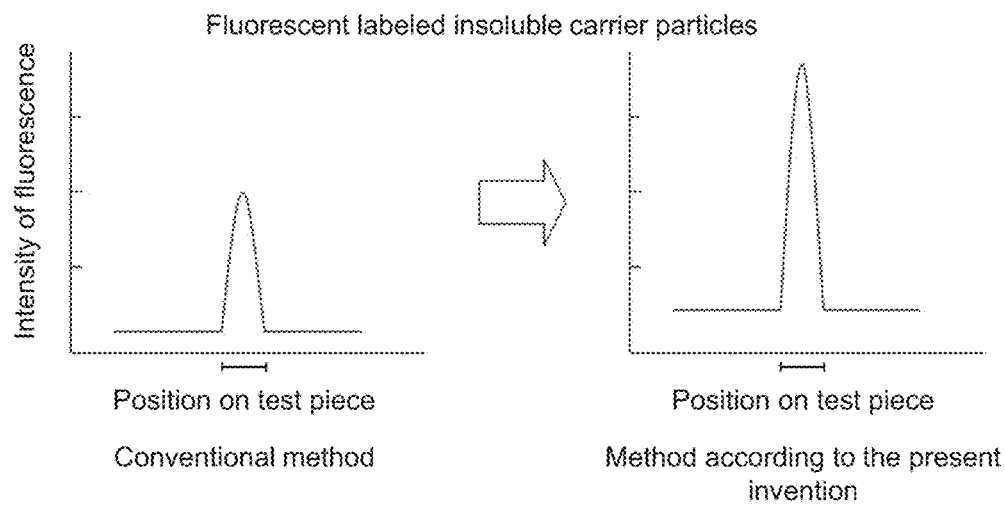
FIGS. 1A-1B show diagrams illustrating the principle of amplification of detection light when an immunochromatographic test piece provided with a light-reflecting material according to the present invention is used.

Hereinafter, the present invention will be described in detail.

The present invention is a test piece for use in the detection of a substance to be detected by immunochromatography. In the immunochromatography, a test piece on which a ligand that specifically recognizes and bonds to the substance to be detected is bound and a ligand that specifically recognizes the substance to be detected are bonded, insoluble carrier particles are used, the insoluble carrier particles bonds to the substance to be detected, move in the test piece with a fiber structure making use of a capillary phenomenon, bond to a capture substance that specifically bonds to the substance to be detected which is immobilized at a predetermined portion in the test piece resulting in formation of a complex of capture substance-substance to be detected-insoluble carrier particles and accumulation of aggregated insoluble carrier particles at a predetermined portion on the test piece, the test piece including the portion where the insoluble carrier particles are accumulated is irradiated with light, and the accumulation of the aggregated insoluble carrier particles are utilized to detect the presence or absence of the accumulation of the insoluble carrier particles by visual observation or with a detection apparatus using light emitted at the portion on the test piece as detection light, thereby analyzing the presence or absence of the substance to be detected.

In the immunochromatographic test piece according to the present invention, a light-reflecting material is provided on a side of the test piece opposite to a side irradiated with light. When the substance to be detected exists, the insoluble carrier particles are accumulated at the portion where the capture substance is immobilized, namely at the detection portion, on the test piece. By providing the light-reflecting material, the detection light is amplified that is emitted at the detection portion where the insoluble carrier particles on the test piece are accumulated and that is detected with a light detection apparatus or by visual observation. That is to say, the light emitted at the detection portion where insoluble carrier particles on the test piece are accumulated is amplified, or the intensity of light emitted at a portion surrounding and other than the detection portion is amplified as compared with the intensity of light emitted at the detection portion, and, as a result thereof, the intensity of the detection light is amplified. The detection light here means light that is emitted from the test piece after the test piece is irradiated with light and detected with a light detection apparatus or by visual observation. Specifically, by using the immunochromatographic test piece provided with a light-reflecting material, the contrast between the intensity of light emitted at the detection portion where the insoluble carrier particles on the test piece are accumulated and the intensity of light emitted at the portion surrounding and other than the detection portion becomes large, and, as a result thereof, the presence of the insoluble carrier particles accumulated at the detection portion can be detected. The "light emitted at the detection portion where the insoluble carrier particles on the test piece are accumulated" in the present invention includes the light emitted from the insoluble carrier particles themselves accumulated at the detection portion, the light reflected at the detection portion, or the light which is reflected at the light-reflecting material provided on a side of the test piece opposite to a side irradiated with light and is detected through the detection portion. Moreover, the "light emitted at a portion surrounding and other than the detection portion on the test piece" includes the light reflected at a portion surrounding the detection portion, namely light reflected at a portion where the insoluble carrier particles on the test piece are not accumulated, or the light that is reflected at the light-reflecting material provided on the side of the test piece opposite to the side irradiated with light and passes through the portion other than the detection portion.

The insoluble carrier particles means particles that are per se insoluble to liquid and are to become carriers to which an antigen or antibody is bonded and which retains the antigen or antibody. In the present invention, latex particles for use in the technological fields such as a test drug can be used. The latex particles means particles that form an emulsion by being dispersed in water in a colloidal form. The material of the particles are not particularly limited, however materials for solid phase carriers to which proteins such as an antibody, an antigen, a ligand, and a receptor are bonded and which are used in technical fields such as a test drug can be used. Examples of the material include styrene copolymers such as polystyrene, styrene-acrylic acid copolymers, resins such as polycarbonate, polymethylene methacrylate (PMMA), and polyvinyl toluene, and silica, cellulose, and so on. Among these, styrene-based particles are preferable. The styrene-based particles mean polystyrene or copolymers of styrene or styrene derivatives with polymerizable unsaturated carboxylic acid, polymerizable unsaturated sulfonic acids or the like. Examples of the styrene derivative include chloromethylstyrene, divinylbenzene, and so on, examples of the polymerizable unsaturated carboxylic acid include acrylic acid, methacrylic acid, and so on, and examples of the polymerizable unsaturated sulfonic acid include sodium styrene sulfonate and so on. In the present invention, styrene-based latex particles are referred to as polystyrene latex particles.

The particle diameter of the particles to be used is 10 nm to several hundred nm, preferably 30 nm to 500 nm.

The insoluble carrier particles include fluorescent labeled insoluble carrier particles that are labeled with a fluorescent dye and colored insoluble carrier particles that are colored with a coloring dye.

As the fluorescent labeled insoluble carrier particles, insoluble carrier particles labeled with a fluorescent dye by bonding the fluorescent dye as a fluorescent labeling agent to the insoluble carrier particles can be used. The kind of the fluorescent dye that is bonded to the insoluble carrier particles is not limited, and the fluorescent dyes used in the field of test drugs, and so on can be used.

Examples of the fluorescent dye for use in fluorescent labeling include organic fluorescent dyes having, as a basic skeleton, fluorescein, rhodamine, coumarin, Cy dye, Alexa® Fluor, EvoBlue, oxazine, Carbopyronin, naphthalene, biphenyl, anthracene, phenenthren, pyrene, carbazole, and so on, and derivatives of the organic fluorescent dyes. Moreover, rare earth complexes such as europium ($EU^{3+}$) chelates and terbium ($Tb^{3+}$) chelates can also be used. As a europium ($EU^{3+}$) chelate, ATBTA-$EU^{3+}$ and so on having an amino group can be used. Furthermore, fluorescent proteins such as Green Fluorescent Protein (GFP) can also be used.

Labeling of the insoluble carrier particles with the fluorescent dye can be conducted in such a way that a functional group such as a carboxyl group, an amino group, a sulfonate group, a thiol group, and an aldehyde group is introduced in the insoluble carrier particles in advance, a functional group is introduced also in the florescent dye, and the fluorescent dye is bonded to the insoluble carrier particles through bonding reaction between functional groups. For example, the amino group and the carboxyl group can be bonded through an amide bond, or thiol groups can be bonded to each other through a disulfide bond. Moreover, functional groups can be bonded to each other using a crosslinking reagent. Examples of the crosslinking reagent include N-hydroxysuccinimide esters, maleimide, EDAC (N-(3-dimethylaminopropyl)-N'-ethylcarbodiimide hydrochloride), glutaraldehyde, and so on. Moreover, when a rare earth complex is used as a fluorescent dye, ATBTA-$EU^{3+}$ or the like in which an amino group is introduced may be used. Furthermore, when a fluorescent protein is used, the bond between functional groups may be utilized, however the fluorescent protein can also be bonded to insoluble carrier particles making use of physical adsorption. As a fluorescent dye in which an amino group or carboxyl group is introduced, commercially available fluorescent dyes can be used.

The fluorescent dyes that can be used in the present invention are shown below. The excitation wavelength (nm) and fluorescence wavelength (nm) of each fluorescent dye are shown as excitation wavelength/fluorescence wavelength in the parenthesis. The excitation wavelength and fluorescence wavelength become shorter or longer depending on the measurement condition, or the like. The excitation wavelength and fluorescence wavelength can be measured within a range of ±several tens of nm, for example ±25 nm from the following wavelengths. The fluorescent dyes are only a few examples and are not limited thereto, and the various fluorescent dyes can be used based on their fluorescence wavelengths.

Organic Fluorescent Dyes

Dylight® 405 (400/420), DY-405 (400/420), Cascade Blue (400/420), Alexa Fluor® 405 (401/421), AMCA (353/440), Alexa-350 (346/442), AMCA-X (347/447), Pacific Blue™ (405/455), Marine Blue (365/460), DY-415 (418/467), Royal Blue (426/480), ATTO425 (436/484), Cy™ 2 (489/505), ATTO465 (453/508), DY-475XL (492/509), Northern Lights™ 493 (493/514), BODIPY® 505/515 (505/515), DY-490 (490/516), DyLight® 488 (493/518), Alexa-488 (495/519), 5-FITC (494/519), FAM (495/520), DY-495-X5 (495/520), DY-495 (493/521), Fluorescein (494/521), FITC (Fluorescein isothiocyanate) (498/522), ATTO488 (501/523), HiLyte Flour™ 488 (499/523), MFP488 (501/523), ATTO495 (495/527), OG-488 (496/524), Rhodamine110 (500/525), OG-514 (511/530), Oyster® 500 (505/530), Spectrum Green (497/538), Alexa-430 (431/541), ATTO520 (525/545), ATTO532 (532/553), Cas Y (402/554), Alexa-532 (530/554), DY-500XL (505/555), DY-485XL (485/560), Alexa-555 (555/565), HiLyte Plus555 (552/567), DyLight549 (550/565), HiLyte Fluor555 (553/568), Cy3 (550/565), Dylight547 (557/570), Rhodamine (550/570), TRITC (550/570), DY-548 (558/572), DY-554 (551/572), DY-555 (547/572), Alexa Fluor 546 (556/573), DY-556 (548/573), Northern Lights557 (557/574), Oyster 550 (555/574), 5-TAMRA (547/574), DY-505-X5 (505/574), DY-547 (557/574), Oyster 556 (562/575), DY-549 (560/575), Alexa-546 (556/575), ATTO550 (554/576), PE (488/578), B-PE (545/578), R-PE (566/578), DY-560 (559/578), TAMRA (555/580), Tetramethyl rhodamine (552/578), RITC/TMR (555/580), MFP555 (560/585), Spectrum Orange (559/588), DY-510XL (509/590), Rhodamine B (570/590), ATTO565 (563/592), Cy3.5 (581/596), ROX (Rhodamine Red X) (587/599), DY-590 (580/599), 5-ROX (573/602), Alexa-568 (578/603), BODIPY 580/605 (580/605), Spectrum Red (587/612), ECD (488/613), Texas Red® (596/615), DyLight594 (593/618), Alexa Flour594 (590/619), HiLyte Fluor TR (591/622), ATTO590 (594/624), MFP590 (597/624), DY-610 (610/630), DY-480XL (500/630), ATTO610 (615/634), DY-615 (621/641), C-Phycocyanin (616/647), ATTO620 (619/643), Alexa-633 (632/647), Phycocianin (620/650), DY-481XL (515/650), ATTO633 (629/657), DY-630 (636/657), DY-632 (637/657), DY-633 (637/657), MFP631 (633/658), DyLight633 (638/658), Northern Lights637 (637/658), DY-631 (637/658), DY-634 (635/658), APC (Allophycocyanin) (650/660), APC-XL (650/660), DY-520XL (520/664), Alexa-647 (650/668), Cy5 (643/667), DY-521XL (523/668), Oyster 645 (650/669), Quantum Red (488/670), DY-635 (645/671), DY-636 (645/671), DY-647 (653/673), DyLight647 (652/673), HiLyte Fluor (653/647), DyLight649 (646/674), HiLyte Plus647 (649/674), Oyster650 (655/674), DY-648 (653/674), DY-650 (653/674), PerCP (488/675), DY-652 (654/675), DY-649 (655/676), DY-651 (656/678), Oyster656 (662/679), ATTO655 (663/684), Alexa-660 (663/690), Cy5.5 (675/694), DY-677 (673/694), DY-678 (674/698), HiLyte Fluor680 (678/699), DY-675 (674/699), DY-676 (674/699), IRDye® 700DX (689/700), Alexa-680 (679/702), DY-681 (691/708), DY-680 (690/709), DY-682 (690/709), DyLight680 (682/715), Alexa Fluor700 (702/723), DY-700 (707/730), DY-701 (706/731), DY-730 (732/758), DY-732 (736/759), DY-734 (736/759), DY-731 (736/760), DY-752 (748/772), DY-750 (747/776), DyLight750 (752/778), HiLyte Fluor750 (751/778), DY-749 (752/778), HiLyte Plus750 (751/779), DY-751 (751/779), DyLight800 (770/794), IRDye800CW (774/800), DY-780 (782/800), DY-781 (783/800), DY-782 (784/800), DY-776 (771/801), DY-777 (771/801), IRDye800 (778/806), and so on.

Rare Earth Complexes

ATBTA-EU$^{3+}$ (335/616), and so on.

Fluorescent Proteins

Sirius (355/424), CFP (452/505), AcGFP (475/505), EGFP (488/509), EYFP (513/527), YFP (514/527), ZsYellow (529/539), mOrange (548/562), DsRed2 (563/582), AsRed2 (576/592), mRFP1 (584/607), mCherry (587/610), HcRed (588/618), mRasberry (598/625), mPlum (590/649), and so on.

Moreover, insoluble carrier particles made of a substance that can emit fluorescence can also be used. Examples of such particles include particles consisting of $M^IM^{II}O_4$ or $M^IAl_5O_{12}$ ($M^I$ represents yttrium (Y), lanthanum (La), or gadolinium (Gd) and $M^{II}$ represents niobium (Nb), phosphorus (P), or vanadium (V)) in which a rare earth element such as europium (Eu) or terbium (Tb) is activated, and insoluble carrier particles described in Japanese Patent Publication (Kokai) No. 2012-32263 can be used. In the present invention, these insoluble carrier particles made of the substance that can emit fluorescence are also included in the insoluble carrier particles that are labeled with a fluorescent dye.

Fluorescent labeled insoluble carrier particles, when irradiated with the excitation light as irradiation light, are excited to emit fluorescence having a wavelength different from the wavelength of the excitation light. Accordingly, when the fluorescent labeled insoluble carrier particles are used, the light emitted from the fluorescent dyes is detected as detection light. That is to say, when the fluorescent labeled insoluble carrier particles are used, the detection light emitted at the detection portion where the insoluble carrier particles are accumulated means fluorescence emitted from the fluorescent dye.

In the case where the fluorescent labeled insoluble carrier particles are used in conducting a test using a test piece provided with a light-reflecting material, when the test piece including a detection portion where the insoluble carrier particles are accumulated is irradiated with the excitation light as irradiation light, the excitation light excites the fluorescent dyes of the fluorescent labeled insoluble carrier particles. Moreover, part of the irradiation light once reaches the light-reflecting material and is reflected to excite the fluorescent dyes of the fluorescent labeled insoluble carrier particles. Fluorescence is emitted from the fluorescent dyes irradiated with the excitation light and is detected. Furthermore, part of the emitted fluorescence is reflected at the light-reflecting material and is detected. As a result thereof, the intensity of the detection light being fluorescence is amplified.

Colored insoluble carrier particles are visible range colored insoluble carrier particles, and the visible range colored insoluble carrier particles mean insoluble carrier particles that are colored in a color so that a person can visually recognize the color. The visible range colored insoluble carrier particles reflect visible rays having a particular wavelength, thereby making it possible for a person to recognize the color by the reflected visible rays. Visible rays are rays having a wavelength of about 380 nm to about 750 nm. The color of the colored particles is represented by hue as chromatic color, the hue includes red, orange, yellow, green, blue, violet, and so on, and each color is recognized by a person as being colored as such by reflecting the following visible rays having particular wavelengths shown below.

Red 620 to 750 nm
Orange 590 to 620 nm
Yellow 570 to 590 nm
Green 495 to 570 nm
Blue 450 to 495 nm
Violet 380 to 450 nm The visible range colored insoluble carrier particles can be produced by dying the particles with a dye of each color. Dyeing with a dye may be dyeing on the surface of the particles, however, in order to prevent detachment of the dye, it is preferable to dye the inside of the particles as well as the surface by impregnating the particles with the dye. Moreover, dyeing with a single dye can be conducted, however visible range colored insoluble carrier particles colored in arbitrary color can be obtained by dyeing with a plurality of dyes. For example, colored insoluble carrier particles of each color such as red particles, blue particles, green particles, yellow particles, and pink particles can be produced. Publicly known dyes that can be used in coloring of resins and so on can be used, and coloring can be conducted using a dyestuff or a pigment such as, for example, Sudan Blue, Sudan III, Sudan Red IV, Quinizarine Green, and Oil Orange. Moreover, particles made of various materials and colored in various colors are sold on the market, and such colored insoluble carrier particles sold on the market can also be used.

The visible range colored insoluble carrier particles reflect the light in the above-described wavelength range according to the color, and, on the other hand, absorb the light in a wavelength range that is in a complementary color relationship with the light in the above-described wavelength range. For example, red insoluble carrier particles absorb light of color that is in a complementary color relationship with red. The wavelength of red light is approximately 620 to 750 nm. The color that is in a complementary color relationship with red is the color of from blue to green, the wavelength of blue light is approximately 450 to 495 nm, and the wavelength of green light is approximately 495 to 570 nm. Moreover, blue insoluble carrier particles absorb light of color that is in a complementary color relationship with blue. The wavelength of blue light is approximately 450 to 495 nm. The color that is in a complementary color relationship with blue is the color of from orange to red, the wavelength of orange light is approximately 590 to 620 nm, and the wavelength of red light is approximately 620 to 750 nm.

When the colored insoluble carrier particles are used in the present invention, it is desirable that the colored insoluble carrier particles be irradiated with the light in the wavelength range that can be absorbed by the colored insoluble carrier particles, namely the light of color in the wavelength range that is in a complementary color relationship with the color of the colored insoluble carrier particles, in order to enhance the contrast between the intensity of light emitted from the detection portion where the colored insoluble carrier particles on the test piece are accumulated and the intensity of light emitted from the portion surrounding and other than the detection portion. As a result thereof, when the irradiation light reaches the colored insoluble carrier particles, most of the light is absorbed instead of being reflected, and the intensity of the reflected light of irradiation light is attenuated. On the other hand, the light that reaches the portion which is surrounding and other than the detection portion and at which colored insoluble carrier particles are not accumulated is transmitted through the test piece without being absorbed, and reaches the light-reflecting material to be reflected. Part of the reflected light is absorbed further by the colored insoluble carrier particles or shielded by the colored insoluble carrier particles. Accordingly, the reflected light of irradiation light is attenuated at the detection portion where the insoluble carrier particles are accumulated, and the detection light emitted at the portion surrounding and other than the detection portion is amplified. In other words, the reflected light at the detection portion becomes weak, and the reflected light at the portion surrounding and other than the detection portion becomes strong. When the colored insoluble carrier particles are used, the light emitted from the detection portion where the insoluble carrier particles are accumulated and the light emitted from the portion surrounding and other than the detection portion mean the reflected light of irradiation light. Accordingly, the wavelength of the irradiation light and the wavelength of the reflected light are the same.

Figure 1B:
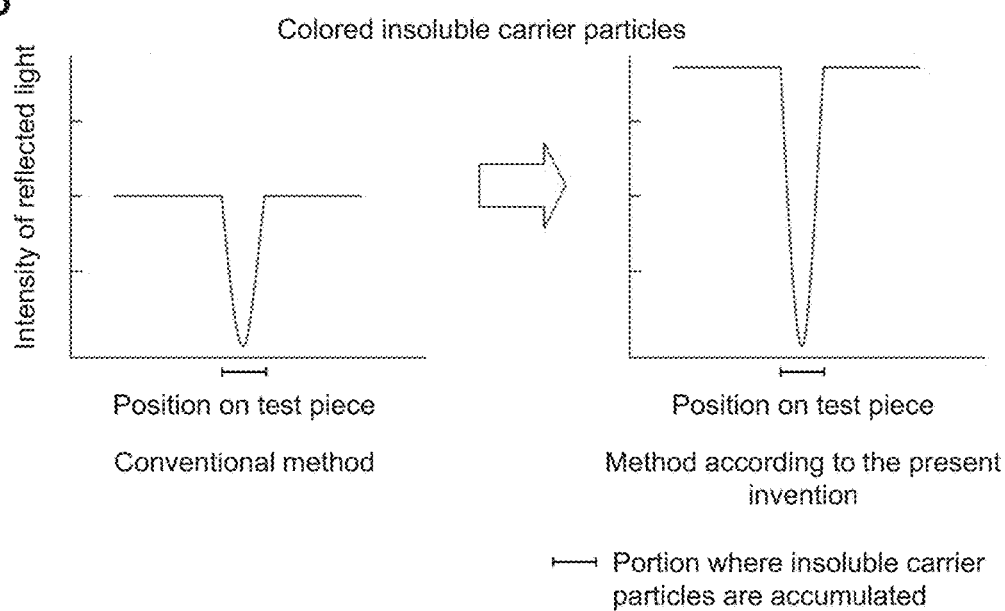

FIGS. 1A-1B show the principle of amplification of detection light when an immunochromatographic test piece provided with a light-reflecting material according to the present invention is used. FIG. 1A shows a case where fluorescent labeled insoluble carrier particles are used, and FIG. 1B shows a case where colored insoluble carrier particles are used. Moreover, the graphs in the figures show a position on the test piece in the horizontal axis and the intensity of light detected at a position on the test piece in the vertical axis. The intensity of light in FIG. 1A that shows the case where the fluorescent labeled insoluble carrier particles are used is the intensity of fluorescence, and the intensity of light in FIG. 1B that shows the case where the colored insoluble carrier particles are used is the intensity of reflected light. Bars below the horizontal axes in the figures show a portion where the insoluble carrier particles are accumulated. Moreover, in the figures, the conventional method is a method in which an immunochromatographic test piece not provided with a light-reflecting material is used, and the method according to the present invention is a method in which an immunochromatographic test piece provided with a light-reflecting material is used. When the fluorescent labeled insoluble carrier particles are used, the fluorescence becomes strong at the portion where the insoluble carrier particles are accumulated as shown in FIG. 1A, however the intensity of fluorescence at the portion is amplified in the method according to the present invention when compared with the intensity of fluorescence in the conventional method. Moreover, when the colored insoluble carrier particles are used, the reflected light of irradiation light is attenuated at the portion where the insoluble carrier particles are accumulated due to an influence of the presence of the insoluble carrier particles and the reflected light becomes strong at the portion surrounding and other than the portion where insoluble carrier particles are accumulated as shown in FIG. 1B. Since the reflected light becomes stronger at the portion surrounding and other than the portion where insoluble carrier particles are accumulated in the method according to the present invention when compared with the reflected light in the conventional method and the situation is left unchanged in which the reflected light of irradiation light at the portion where insoluble carrier particles are accumulated is attenuated, the intensity of the reflected light is amplified at the portion surrounding and other than the portion where the insoluble carrier particles are accumulated, resulting in amplification of the detection light.

The immunochromatographic test piece according to the present invention is made of a porous water-absorbing material and has a member made of a material in which a specimen sample solution can move due to a capillary phenomenon, and the member is called a membrane. The position where the fluorescent labeled insoluble carrier particles or colored insoluble carrier particles are accumulated is called a detection portion, and the membrane includes a detection portion where a capture substance that can bond to a substance to be detected is immobilized. The membrane is made of a material consisting of nitrocellulose, cellulose acetate, nylon, polyethersulfone, polyvinyl alcohol, polyester, glass fiber, polyolefin, cellulose, or mixed fiber thereof, and is preferably made of a nitrocellulose membrane. The thickness of the membrane is not particularly limited, however is preferably about 100 to about 200 µm. Moreover, the membrane is used as a rectangular strip, and the size is not particularly limited, however is usually about 3 mm to 9 mm × about 40 mm to 60 mm.

At the detection portion on the membrane, a ligand that can specifically bond to a substance to be detected to capture the substance to be detected is immobilized. The detection portion is sometimes referred to as the capture portion. At the detection portion, the ligand is immobilized, for example, in a line shape. The "portion surrounding and other than the detection portion on the test piece" in the present invention means a portion that is adjacent to the detection portion and is on the test piece. When the substance to be detected is an antigen, the ligand that bonds to the substance to be detected is typically an antibody that specifically bonds to the antigen, and when the substance to be detected is an antibody, the ligand is an antigen to which the antibody specifically bonds. Besides, examples of the combination of the substance to be detected and the ligand include the combination of a receptor and a ligand, the combination of a ligand and a receptor, and so on. The immunochromatography usually means a test method that makes use of the bond of an antibody and an antigen, however the immunochromatography in the present invention is interpreted in a broad sense and includes a test method using a combination of a substance to be detected and a ligand other than the combination of an antigen and an antibody. Hereinafter, the test method using a combination of an antigen and an antibody will be described. When the substance to be detected is an antigen, an antibody that specifically recognizes the antigen may be immobilized, and when the substance to be detected is an antibody, an antigen that the antibody specifically recognizes may be immobilized. The antibody or antigen may be immobilized, for example, in a line shape or a dot shape, preferably in a line shape. Immobilization can be conducted by a publicly known method for immobilizing a protein in a solid phase such as a nitrocellulose membrane. Examples of the method include a method by use of adsorption, a method by use of chemical bonding that makes use of a functional group such as an amino group and a carboxyl group, and so on. As an antibody, a purified polyclonal antibody or monoclonal antibody is used. As an antigen, a purified natural antigen or recombinant antigen is used.

To the test piece on which the detection portion where the antigen or antibody is immobilized exists, a mixture of a liquid sample containing a substance to be detected and insoluble carrier particles to which an antibody or antigen that bonds to the substance to be detected is bonded is added at a portion other than the detection portion on the test piece, and thereby the insoluble carrier particles and the substance to be detected move on the test piece due to a capillary phenomenon while forming a complex through antigen-antibody reaction. The substance to be detected that has bonded to the insoluble carrier particles through the antigen or antibody bonds to the antibody or antigen that is immobilized at the detection portion to form a complex of immobilized antibody or immobilized antigen-substance to be detected-insoluble carrier particles at the detection portion. The presence of the insoluble carrier particles can be detected by irradiating the test piece with light and measuring light emitted at the detection portion on the test piece or at the portion surrounding and other than the detection portion on the test piece, and, as a result thereof, the presence or absence of the substance to be detected can be detected.

A control-displaying portion may further exist on the membrane. The control-displaying portion is a portion showing that a test is correctly conducted. For example, the control-displaying portion exists on the downstream side of the detection portion, and emits a signal by coloration or the like when the specimen sample passes through the detection portion to reach the control-displaying portion. At the control-displaying portion, a substance that bonds to a ligand that is bonded to insoluble carrier particles may be immobilized or a reagent such as a pH indicator that changes color when the specimen sample reaches the reagent may be immobilized.

The immunochromatographic test piece according to the present invention may further include a sample addition portion, an absorption band, or a labeled portion.

The sample addition portion is a portion where a specimen sample solution is added, and the specimen sample solution may directly be added on the membrane, however a pad of non-woven fabric or the like made of a water-absorbing material such as, for example, sponge and glass fiber may be provided on the test piece, and the specimen sample solution may be added at the portion. When the pad is used, the pad can be called a sample pad. It is preferable to provide the sample addition portion at one end on the test piece.

The absorption band is also called an absorption pad portion, and is provided on one end that is other than the sample addition portion of the immunochromatographic test piece according to the present invention, and facilitates the flow of the sample liquid on the test piece by absorbing the sample liquid that moves on the test piece after being added to the sample addition portion. The absorption band is made of a water-absorbing material so as to be capable of absorbing a large amount of solution, and, for example, non-woven fabric or the like made of cellulose, glass fiber, or the like. Moreover, the size is not particularly limited, but is usually 3 mm to 15 mm×10 mm to 40 mm, and the thickness is about 0.5 mm to about 3 mm.

The labeled portion is a portion where a fluorescent labeled insoluble carrier or a colored insoluble carrier is contained. As the labeled portion, a material of non-woven fabric or the like made of a water-absorbing material such as, for example, sponge and glass fiber is used, the size is not particularly limited, but is usually 3 mm to 10 mm×3 mm to 10 mm, the thickness is about 0.5 mm to about 3 mm, and insoluble carrier particles are contained in a dried state. When labeled insoluble carrier particles are contained in the water-absorbing material and used as the labeled portion, the labeled portion can be called a conjugate pad. In order to prepare the labeled portion, the water-absorbing material may be impregnated with insoluble carrier particles and dried. When the side of the sample addition portion is defined as the upstream side and the side of the absorption band is defined as the downstream side in the case where the specimen sample solution flows on the test piece from the sample addition portion to the absorption band, the labeled portion may be provided on the downstream side of the sample addition portion and on the upstream side of the detection portion. In this case, the sample pad at the sample addition portion may not necessarily make contact with the conjugate pad at the labeled portion.

When a liquid sample is added to the sample specimen portion on the test piece, the liquid sample moves to the labeled portion due to a capillary phenomenon, the insoluble carrier particles contained in the labeled portion dissolves in the liquid sample, and the antigen or antibody that is bonded to the insoluble carrier particles bonds to the substance to be detected in the liquid sample and moves downstream on the membrane of the test piece while forming a complex. The substance to be detected that is bonded to the insoluble carrier particles through the antigen or antibody bonds to the antibody or antigen immobilized at the detection portion, thereby the complex of the insoluble carrier particles and the substance to be detected is captured by the antibody or antigen immobilized at the detection portion, and the insoluble carrier particles are accumulated at the detection portion. The rest of the liquid sample passes through the detection portion and is absorbed by the absorption band.

The test piece according to the present invention may include a backing sheet. The backing sheet can also be referred to as a support sheet, and is used for lining the membrane, the sample addition portion, the absorption band, and the labeled portion. The membrane, the sample addition portion, the absorption band, and the labeled portion may stick to the backing sheet. The backing sheet is a sheet made of a plastic or the like that liquid does not permeate, supports the membrane and other members such as the sample addition portion so as to be kept in a constant structure or strength, and can prevent the sample specimen from flowing out from the test piece. When the backing sheet exists, a test piece including the backing sheet is also referred to as a test piece. The backing sheet may exist between the membrane and the light-reflecting material that will be described later, or may exist on the underside of the light-reflecting material. When the backing sheet exists on the underside of the light-reflecting material, the backing sheet may be made of a raw material that does not transmits light, however when the backing sheet exists between the membrane and the light-reflecting material, the backing sheet is required to be made of a raw material that transmits light without remarkable attenuation, such as, for example, a transparent plastic.

The immunochromatographic test piece according to the present invention may be stored in a storage container, and the degradation caused by, for example, ultraviolet rays or moisture in the air can be prevented by the storage container. Moreover, when a specimen sample that can contain an infectious microorganism such as a virus or bacterium is used, the storage container makes it possible to prevent an examiner who conducts an assay from making contact with these microorganisms. For example, a resin-made case having an appropriate size may be used as a storage container to store the device according to the present invention in the case. Moreover, the surface of the test piece on which an antigen or antibody is immobilized may be covered (top laminate) with a resin-made film or the like. The storage container and the test piece stored therein are referred to as an immunochromatographic device as an integrated unit.

In the immunochromatographic test piece according to the present invention, a light-reflecting material is provided on the side opposite to the side irradiated with light on the test piece including the detection portion where insoluble carrier particles are accumulated, thereby the irradiation light that is transmitted through the test piece under normal circumstances reaches the light reflecting material to be reflected.

As the light reflecting material, any material can be used as long as the material that can reflect the irradiation light. Moreover, the light reflecting material may be formed from a substance that reflects light, or a material that does not reflect light under normal circumstances may be covered with a material that reflects light. Examples of the substance that reflects light include inorganic substances such as metals, glass, mica, and silica. The substance that reflects light is preferably a metal, and it is preferable that the light-reflecting material itself is made of a metal. It is preferable that the metal having a high light reflectance is preferable, and examples of the preferable metal include aluminum, tantalum, nickel, tungsten, copper, brass, nickel-titanium, gold, platinum, and so on, and alloys thereof. The surface of the light-reflecting material may be treated so as to have a gloss to perform specular reflection of light, or so as to leave roughness on the surface to perform diffusion reflection of light, however it is preferable that the surface of the light-reflecting material is treated so as to perform specular reflection. Moreover, examples of covering the material that does not reflect light under normal circumstances with the material that reflects light include a light-reflecting material in which the surface formed from a substance such as a resin is coated with a metal. Furthermore, the surface may also be coated with a metal powder to form a metal film. Forming a metal thin film on the surface can be conducted by a method such as plating, sputtering, or vapor deposition. Moreover, a thick film (for example, film thickness of 5 to 20 μm) can also be formed by electroless nickel-phosphorus plating.

Figure 2:
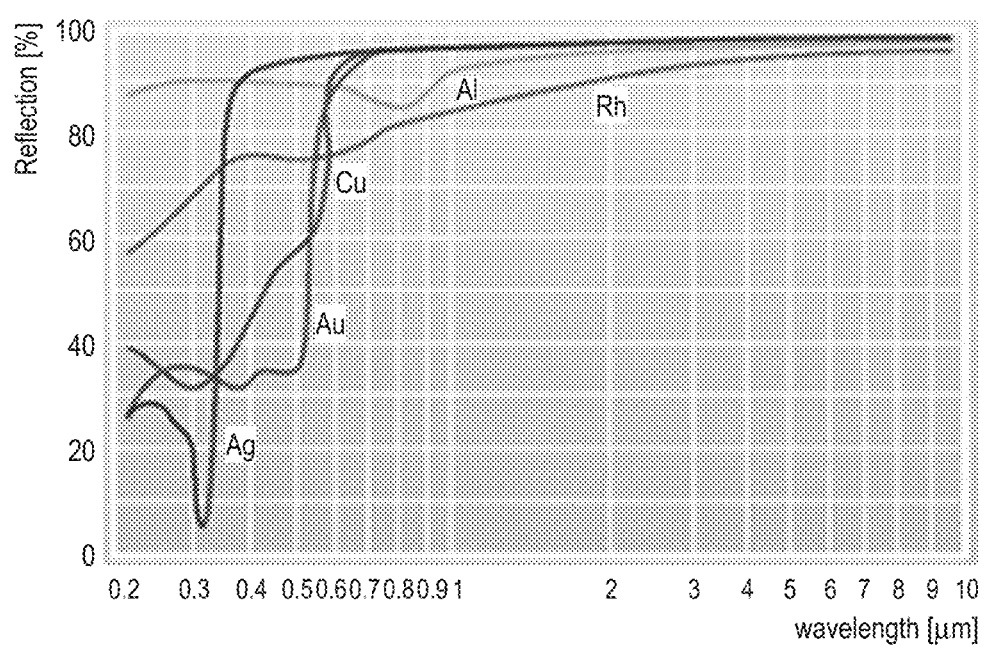
FIG. 2 is a graph showing total reflectance of various metals.

The wavelength of light where the reflectance is high is different depending on the metal. Accordingly, when a metal is used as a light-reflecting material, the kind of metal may be selected according to the wavelength of irradiation light. That is to say, the metal having a high reflectance to light at the wavelength of irradiation light with which the detection portion is irradiated may be selected. The reflectance of a metal to the wavelength of light can be determined by measuring a reflection spectrum of the metal with a spectrophotometer or the like. Accordingly, the reflection spectrum of each metal may be measured to use the metal having a high reflectance at the wavelength of irradiation light to be used may be used. FIG. 2 shows the total reflectance of metals such as aluminum and copper (the figure is quoted from MacLeod. "Thin film optical filters", A. Hilger, London, 1985). In FIG. 2, the horizontal axis shows wavelength, and the vertical axis shows total reflectance. For example, the combination of the wavelength of irradiation light and the metal may be selected with reference to the figure.

For example, the combination of the wavelength and the metal where the total reflectance with an angle of incidence of 45° is 80% or more, preferably 85% or more, further preferably 90% or more, particularly preferably 95% or more may be used.

For example, aluminum has a total reflectance of 85% or more in a range from 250 nm to 1000 nm and therefore can be used to irradiation light of 250 nm to 1000 nm. Moreover, copper has a total reflectance of 90% or more to the light having a wavelength of 600 nm or more, and therefore when the irradiation light of 600 nm to 1000 nm is used, copper may be used.

In addition, the immunochromatographic test piece is used once and then thrown away, therefore a metal that is available at a low cost is preferable in order to lower production costs of the apparatus, and from this standpoint, aluminum and copper are preferable.

In the immunochromatographic test piece, it is preferable to use a sheet-like or foil-like light-reflecting material. Aluminum foil and copper foil can be used as the light-reflecting material, and commercially available aluminum foils and copper foils may be used.

When the test piece transmits the irradiation light with which the detection portion of the immunochromatographic test piece is irradiated, the light-reflecting material is used for reflecting the irradiation light. Accordingly, the light-reflecting material is provided on the side that is irradiated with light to the immunochromatographic test piece, namely on the side opposite to the side where a light source exists. Usually, the immunochromatographic test piece, when used, is placed horizontally with the face on which the antibody or antigen is immobilized turned upside. Accordingly, the light-reflecting material is provided on the underside of the immunochromatographic test piece. In the invention of the present application, the position where the light-reflecting material is provided is referred to as the underside of the test piece, however the underside of the test piece means the side opposite to the side that is irradiated with light, not determined by the upper or lower side base on the direction in which a gravitational field acts.

The light-reflecting material is provided at least on the underside or lower portion of the detection portion on the test piece. The size of the light-reflecting material may be the size by which at least the detection portion on the test piece can be covered, however the light-reflecting material the size of which is larger than the size of the detection portion so that the irradiation light that is transmitted through the portion surrounding and other than the detection portion may be reflected is preferably used, and, for example, the light-reflecting material having the size covering the whole membrane on the test piece is used.

The light reflecting-material is integrated with the test piece, may also be integrated with the storage container for the test piece, and may be stored together with the test piece in the storage container for the test piece. Moreover, the backing sheet itself may be a light-reflecting material, and, for example, aluminum foil or copper foil may be used as a backing sheet.

FIGS. 3A-3F illustrate embodiment examples in which the position where the light-reflecting material is provided is changed or the shape of the light reflecting material is changed in the immunochromatographic test piece or the immunochromatographic device including a storage container according to the present invention. In FIGS. 3A-3F, a represents an absorption band, b represents a membrane, b' represents a detection portion on the membrane, c represents a conjugate pad, d represents a sample pad, e represents a backing sheet, f represents a light-reflecting material, g represents a backing sheet that transmits light, and h represents a storage container.

Figure 3A:
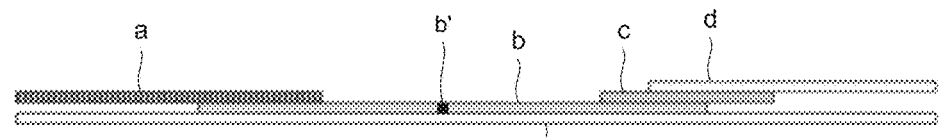
FIGS. 3A-3F show views illustrating a position and shape of a light-reflecting material in an immunochromatographic test piece or device including the light-reflecting material according to the present invention.
Figure 3B:
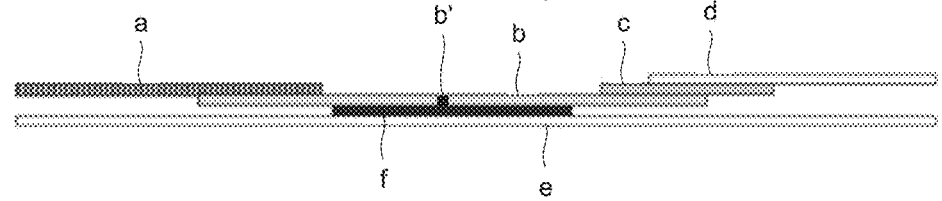
Figure 3C:
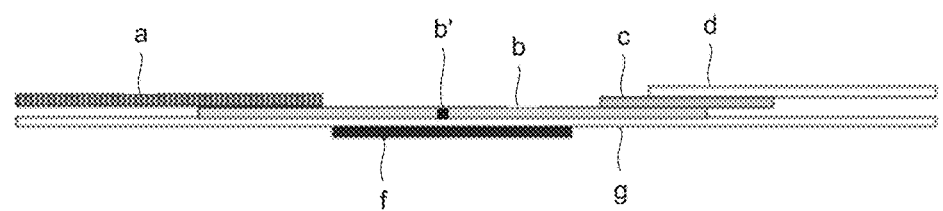
Figure 3D:
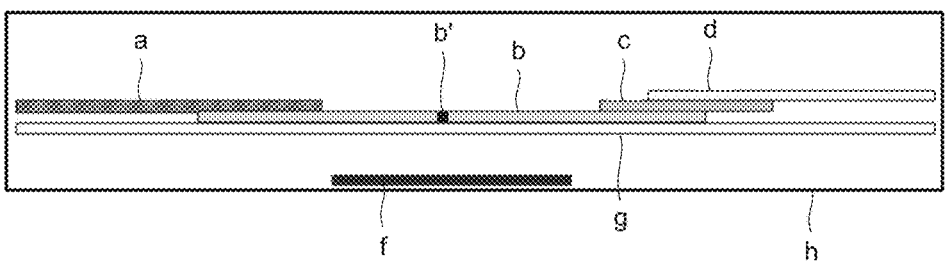
Figure 3E:
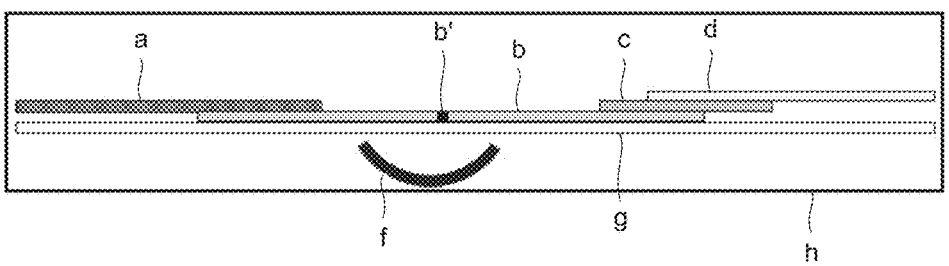
Figure 3F:
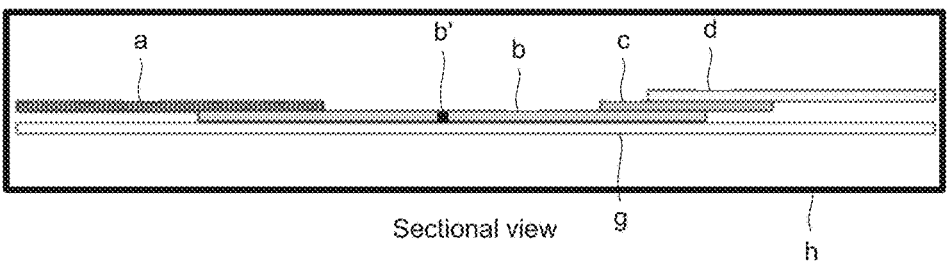

FIG. 3A illustrates an Embodiment Example that is used in the conventional immunochromatography not using a light-reflecting material. FIG. 3B1 and FIG. 3C show views illustrating Embodiment Example 1 and Embodiment Example 2 of the immunochromatographic test pieces provided with a light-reflecting material according to the present invention, and the light-reflecting material is integrated with the test piece. FIG. 3D, FIG. 3E, and FIG. 3F show views illustrating Embodiment Examples 3, 4, and 5 where the test piece stored in s storage container to which a light-reflecting material is attached, the light-reflecting material is stored in the storage container together with the test piece in the devices illustrated in FIG. 3D and FIG. 3E, and the light-reflecting material is integrated with the storage container in the apparatus illustrated in FIG. 3F. In the immunochromatographic test piece illustrated in FIG. 3B, the light reflecting material f is provided on the underside of the detection portion b' of the membrane b so as to make contact with the membrane b, and the backing sheet e is further stuck to the underside of the membrane b. In the immunochromatographic test piece illustrated in FIG. 3C, the backing sheet g is stuck to the underside of the membrane b, and the light-reflecting material f is further provided to the underside of the backing sheet. In the apparatus illustrated in FIG. 3B, the backing sheet e may be a material that shields light, however in the apparatus illustrated in FIG. 3C, the backing sheet g is required to be made of a material that is transparent and transmits light.

FIG. 3D, FIG. 3E, and FIG. 3F illustrate devices in which the test piece is stored in the storage container, and the light-reflecting material f is provided on the inner surface of the storage container h. In the immunochromatographic device illustrated in FIG. 3D, the light-reflecting material f is provided on the inner surface of the storage container h which corresponds to the underside portion of the detection portion b' on the test piece. In the immunochromatographic device illustrated in FIG. 3E, the light-reflecting material f is attached to the position similar to the position in the apparatus illustrated in FIG. 3D, however the light-reflecting material f is processed so as to have a curved surface, and the reflected light is collected at the detection portion b' and the portion surrounding the detection portion b' on the test piece due to the presence of the curved surface. That is to say, the light-reflecting material f in the apparatus illustrated in FIG. 3D has a curved surface by which the reflected light focuses on the detection portion b' and the portion surrounding the detection portion b' on the test piece. The shape of the light-reflecting material is not limited, and may have a hemispherical structure, a semi-cylindrical structure, or a polyhedral structure as long as the irradiation light is reflected so as to efficiently reach the immunochromatographic test piece including a detection portion due to its structure. Furthermore, in the immunochromatographic device illustrated in FIG. 3F, the inner surface itself of the storage container h is a light-reflecting material. In this case, the whole inner surface of the storage container may be a light-reflecting material, or part of the inner surface of the storage container may be a light-reflecting material. Moreover, the storage container itself may be formed from a light-reflecting material such as aluminum or copper, or the inner surface of the storage container may be coated with aluminum or copper.

The substance to be detected and specimen sample which are detected using the immunochromatographic test piece according to the present invention are not limited. For example, as a specimen sample solution, a pharynx or nasal cavity swab, a nasal cavity aspirate, a pharynx or nasal cavity lavage fluid, saliva, serum, blood plasma, whole blood, a suspension of feces, urine, a culture solution, diluted solutions thereof diluted with a buffer solution, and so on can be used. The substance to be detected is also not limited at all, and any substance that is intended to be detected may be used. Examples of the substance to be detected include virus antigens such as influenza viruses, adenoviruses, RS viruses, and Norwalk-like viruses, bacterial antigens such as *Legionella* bacteria, hemolytic *streptococcus*, and MRSA, and antigens such as hormones, and the examples further include antibodies to the above-described bacteria, viruses and so on.

In the detection method using the immunochromatographic test piece according to the present invention, an immunochromatographic test is conducted to irradiate the fluorescent labeled insoluble carrier particles or colored insoluble carrier particles accumulated at the detection portion on the test piece with light.

When the fluorescent labeled insoluble carrier particles are used in an assay using the immunochromatographic test piece according to the present invention, the test piece including the detection portion where the insoluble carrier particles are accumulated are irradiated with the excitation light from above the test piece. The excitation light with which the test piece is irradiated excites fluorescent dyes of the fluorescent labeled insoluble carrier particles accumulated at the detection portion on the test piece to generate fluorescence. Since the light-reflecting material is provided on the side of the test piece opposite to the side irradiated with the excitation light in the immunochromatographic test piece according to the present invention, the excitation light with which the test piece is irradiated is reflected at the light-reflecting material, making it possible to amplify the intensity of the excitation light that reaches the fluorescent dyes of the insoluble carrier particles accumulated at the detection portion. Moreover, part of the fluorescence generated by irradiation of the excitation light is also reflected at the light-reflecting material to be detected as detection light. Therefore, the fluorescent dyes are efficiently excited to generate fluorescence and the intensity of fluorescence emitted at the detection portion on the test piece is amplified. Since the fluorescent dyes do not exist at the surrounding portion that is other than the detection portion and where fluorescent labeled insoluble carrier particles do not exist, the fluorescence is not emitted and the contrast between the fluorescence emitted at the detection portion and the fluorescence emitted at the portion surrounding and other than the detection portion becomes high to amplify the detected light, making it possible to detect the accumulation of the fluorescent labeled insoluble carrier particles at the detection portion on the test piece with high sensitivity. As a result thereof, the detection of a substance to be detected with high sensitivity is made possible.

Measurement of the fluorescence can be conducted using a fluorescence detection apparatus including light irradiation means that irradiates the test piece with the excitation light and light detection means that detects generated fluorescence. As such an apparatus, publicly known fluorescence detection apparatuses can be used. Moreover, an apparatus that detects fluorescence can appropriately be designed by including a portion that stores a device including a test piece or storage container and providing the test piece or device at the portion. Moreover, the measurement of the fluorescence can also be conducted by visual observation. When a particular antigen is measured as a substance to be detected, the concentration of the antigen contained in a specimen sample can be determined from the intensity of the obtained fluorescence in such a way that the intensity of fluorescence to be obtained when the concentration of the antigen is changed is measured in advance to make a calibration curve based on the measured values.

Moreover, when the colored insoluble carrier particles are used, the test piece including the detection portion where insoluble carrier particles are accumulated is irradiated with light from above the test piece. Part of the light with which the test piece is irradiated is absorbed by the colored insoluble carrier particles. Moreover, part of the light with which the test piece is irradiated is transmitted through the test piece and is reflected at the light-reflecting material provided on the side of the test piece opposite to the side irradiated with light. The reflected light, when reaches the colored insoluble carrier particles, is absorbed by the insoluble carrier particles again or shielded by the insoluble carrier particles. On the other hand, the portion surrounding and other than the detection portion where insoluble carrier particles are accumulated is irradiated with part of the light with which the test piece is irradiated and the part of the light with which the test piece is irradiated is transmitted through the test piece to be reflected at the light-reflecting material provided on the side of the test piece opposite to the side irradiated with light to be detected as detection light without reaching the insoluble carrier particles. Therefore, the reflected light of irradiation light is attenuated due to the insoluble carrier particles accumulated on the test piece, the intensity of the light emitted at the detection portion, namely the light to be reflected becomes lowered, and the intensity of the light emitted at the portion surrounding and other than the detection portion where the insoluble carrier particles on the test piece are accumulated, namely the light to be reflected becomes high. As a result thereof, the contrast between the light emitted at the detection portion where the insoluble carrier particles on the test piece are accumulated and the light emitted at the portion surrounding and other than the detection portion where the insoluble carrier particles on the test piece are accumulated becomes high to amplify the detected light, making it possible to detect the accumulation of the colored insoluble carrier particles at the detection portion on the test piece with high sensitivity. As a result thereof, the detection of a substance to be detected with high sensitivity is made possible.

Measurement of the reflected irradiation light can be conducted using a light detection apparatus including light detection means that detects light. As such an apparatus, a reader dedicated to immunochromatography for example can be used. Moreover, the measurement of the reflected irradiation light can also be conducted by visual observation. When a particular antigen is measured as a substance to be detected, the concentration of the antigen contained in a specimen sample can be determined from the intensity of the obtained light in such a way that the intensity of light to be obtained when the concentration of the antigen is changed is measured in advance to make a calibration curve based on the measured values.

Hereinafter, a method for detecting a virus antigen in a serum using the test piece as shown in FIG. 3C according to the present invention and the fluorescent labeled insoluble carrier particles in combination will be described as an example of detection of a substance to be detected using the immunochromatographic test piece according to the present invention.

On the membrane b, the detection portion b' where an antivirus antigen/antibody is immobilized in a line shape exists. The conjugate pad c is impregnated with fluorescent labeled insoluble carrier particles to which antivirus antigen/antibody is bonded, and the conjugate pad c is then dried. A specimen sample liquid containing a virus antigen to be detected is added to the sample pad by several tens of μl to several hundreds of μl. The specimen sample liquid flows from the sample pad to the conjugate pad, and dissolves the insoluble carrier particles with which the conjugate pad is impregnated and dried. When the specimen sample liquid dissolves the insoluble carrier particles and flows downstream, the antivirus antigen/antibody that is bonded to the insoluble carrier particles bonds to a virus antigen to form a complex of insoluble carrier particles-virus antigen. When the complex reaches the detection portion on the membrane, the virus antigen is captured by the antivirus antigen/antibody immobilized at the detection portion and a complex of antivirus antigen/antibody-virus antigen-insoluble carrier particles is formed at the detection portion. The rest of the specimen sample liquid passes through the detection portion to move downstream on the membrane and is absorbed by the absorption band. The fluorescent dyes of the insoluble carrier particles, when irradiated with the excitation light, emit fluorescence. The excitation light that is transmitted through the membrane is reflected at the light-reflecting material provided on the underside of the membrane to excite the fluorescent dyes again and the intensity of fluorescence is amplified.

Also, when the colored insoluble carrier particles are used, a complex of antivirus antigen/antibody-virus antigen-insoluble carrier particles may be formed at the detection portion in the same manner as described above, and the test piece may be irradiated with light.

The present invention further includes an immunochromatographic kit including the immunochromatographic test piece or immunochromatographic device according to the present invention.

EXAMPLES

The present invention will be specifically described by the following Examples, however the present invention is not limited by these Examples. In the description of Examples, % denotes % by weight.

Example 1 Amplification of Detection Light Emitted from Fluorescent Polystyrene Particles with Metal (Aluminum) Foil Provided at Lower Portion of Immunochromatographic Test Piece 1. Mouse IgG purified by affinity chromatography using a protein A column was diluted with purified water so as to be 1.0 mg/mL, fluorescent polystyrene particles (manufactured by Thermo Fisher Scientific Inc.: product name; Fluoro Max) containing a europium (EU') chelate were added thereto so as to be 0.1% to stir, then carbodiimide was added so as to be 1%, and the resultant mixture was further stirred. The supernatant was removed by a centrifugal operation, and the rest of the mixture was resuspended in 50 mM Tris (pH of 9.0) and 3% BSA to obtain mouse-derived antibody-labeled fluorescent polystyrene particles.

2. Immobilization of Anti-Mouse IgG Antibody to Nitrocellulose Membrane

A liquid obtained by diluting anti-mouse IgG antibody with purified water so as to be 1.0 mg/mL was applied in a line shape at a predetermined portion of a nitrocellulose membrane lined with a PET film, and dried at 45° C. for 30 minutes to obtain an antibody-immobilized membrane (hereinafter, denoted as antibody-immobilized membrane).

Figure 4A:
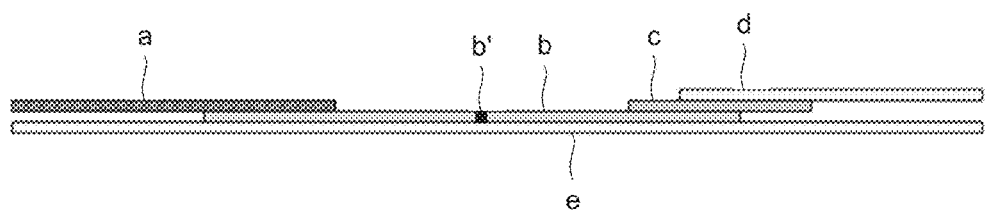
FIGS. 4A-4B show views illustrating a structure of an immunochromatographic test piece including a light-reflecting material according to the present invention and a structure of a conventional immunochromatographic test piece.
Figure 4B:
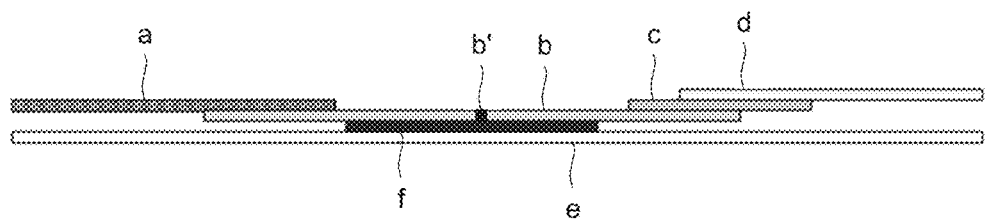

3. Accumulation of Labeled Particles at Immobilized Portion by Immunochromatography The antibody-immobilized membrane obtained in 2, a backing sheet, an absorption band, a conjugate pad, and a sample pad were stuck together to make a test piece, and the test piece not containing a light-reflecting material was denoted as a conventional test piece (FIG. 4A). Moreover, the members were stuck together to make a test peace holding an aluminum foil metal foil as a light-reflecting material under the antibody-immobilized membrane and on the backing sheet, and the test piece including the light-reflecting material was denoted as a test piece of the method according to the present invention (FIG. 4B).

On the sample pad of the test piece, 50 µl of a specimen-suspended liquid (10 mM Tris (pH of 7.0), 3% BSA, and 0.2% Triton X-100) was dropped. After the resultant mixture was left standing for 15 minutes, fluorescence was confirmed by visual observation on a UV transilluminator (Benchtop 2UV transilluminator; manufactured by UVP, LLC).

Figure 5:
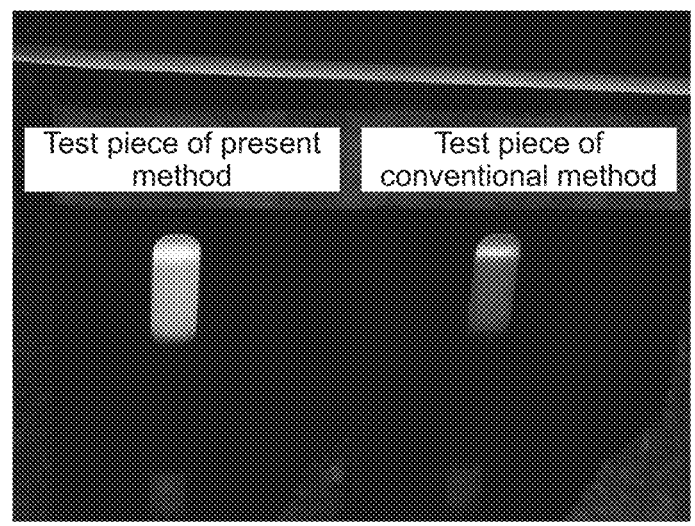
FIG. 5 is a diagram showing fluorescence at a detection portion of an immunochromatographic test piece including a light-reflecting material according to the present invention and at a detection portion of a conventional immunochromatographic test piece.

As a result, the accumulation of the fluorescent polystyrene particles was able to be confirmed on the portion where the antibody was immobilized. It was able to be confirmed that the intensity of the emitted light from the test piece of the method according to the present invention was clearly increased in visual observation when compared with the intensity of the emitted light from the conventional test piece (FIG. 5).

From the above results, it is made possible to amplify the detection light by using the test piece prepared according to the present method. The fluorescence is evaluated by visual observation in the present Example, however it is considered that the fluorescence can be detected with further high sensitivity by detecting the fluorescence with an apparatus.

Example 2 Amplification of Detection Light Emitted from Fluorescent Polystyrene Particles with Various Metal Foils Provided at Lower Portion of Immunochromatographic Test Piece 1. Mouse IgG purified by affinity chromatography using a protein A column was diluted with purified water so as to be 1.0 mg/mL, fluorescent polystyrene particles containing a europium chelate were added thereto so as to be 0.1% to stir, then carbodiimide was added so as to be 1%, and the resultant mixture was further stirred. The supernatant was removed by a centrifugal operation, and the rest of the mixture was resuspended in 50 mM Tris (pH of 9.0) and 3% BSA to obtain mouse-derived antibody-labeled fluorescent polystyrene particles.

2. Immobilization of Anti-Mouse IgG Antibody to Nitrocellulose Membrane

A liquid obtained by diluting anti-mouse IgG antibody with purified water so as to be 1.0 mg/mL was applied in a line shape at a predetermined portion of a nitrocellulose membrane lined with a PET film, and dried at 45° C. for 30 minutes to obtain an antibody-immobilized membrane (hereinafter, denoted as antibody-immobilized membrane).

Figure 6A:
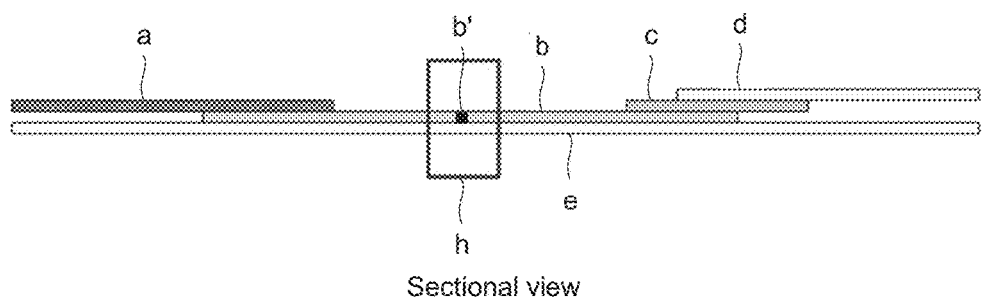
FIGS. 6A-6B show views illustrating a structure of an immunochromatographic test piece including a light-reflecting material according to the present invention and a structure of a conventional immunochromatographic test piece, and also shows cut portions in Example 2.
Figure 6B:
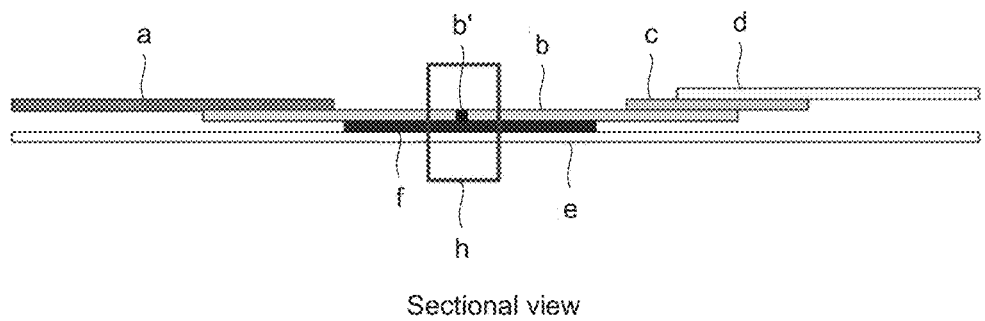

3. Accumulation of Fluorescent Polystyrene Particles at Immobilized Portion by Immunochromatography The antibody-immobilized membrane obtained in 2, a backing sheet, an absorption band, a conjugate pad, and a sample pad were stuck together to make a test piece, and the test piece not containing a light-reflecting material was denoted as a conventional test piece (FIG. 6A). Moreover, the members were stuck together to make a test peace holding a metal (aluminum, copper, and stainless steel) foil as a light-reflecting material under the antibody-immobilized membrane and on the backing sheet, and the test piece including the light-reflecting material was denoted as a test piece of the method according to the present invention (FIG. 6B).

On the sample pad of the test piece, 50 µl of a specimen-suspended liquid (10 mM Tris (pH of 7.0), 3% BSA, and 0.2% Triton X-100) was dropped. After the resultant mixture was left standing for 15 minutes, a portion (h) surrounded by a square in FIGS. 6A-6B in the antibody-immobilizing portion of the test piece was cut and irradiated with irradiation light (365 nm) with a fluorescence plate reader (MTP-650FA MICROPLATE READER; manufactured by CORONA ELECTRIC Co., Ltd.) to measure the intensity of detection light (615 nm) emitted from the fluorescent polystyrene particles.

Figure 7:
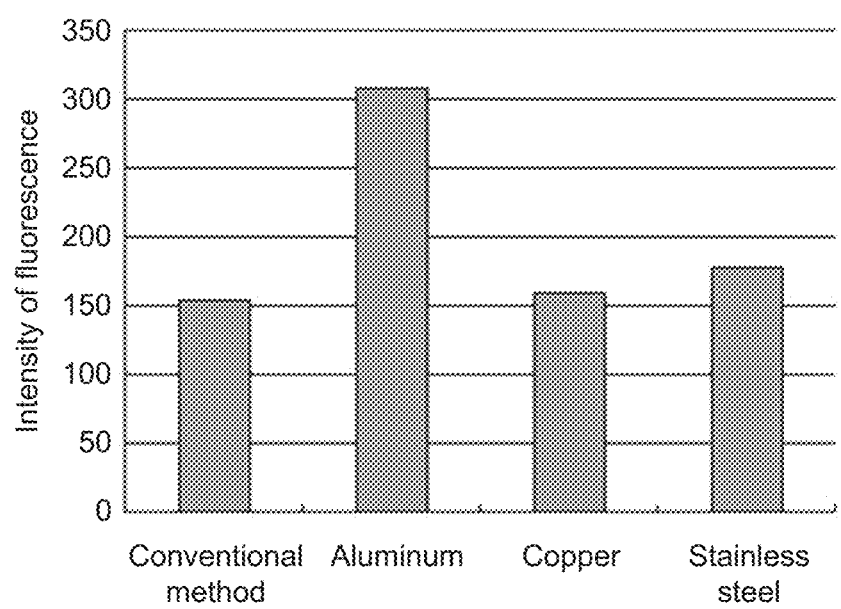
FIG. 7 is a graph showing an effect of reflection when various kinds of metal foils are used as a light-reflecting material.

As a result, the intensity of the emitted fluorescence was clearly amplified by using the aluminum foil as compared with the intensity of emitted fluorescence obtained from the conventional test piece, and amplification was also observed in the cases of copper foil and stainless steel foil. The extent of amplification of detection light was most remarkable in the aluminum foil when comparison was made among the three foils (FIG. 7).

The reflectance specific to a light-reflecting material exists depending on the wavelength (FIG. 2). Aluminum used in the present Example efficiently reflects the irradiation light having a wavelength of 365 nm with a reflectance of about 90%, and, on the other hand, copper reflects the irradiation light having a wavelength of 365 nm with a reflectance of 40% or less.

The fact that aluminum had a larger extent of amplification of detection light than copper in the present Example shows that the reflection efficiency of the light-reflecting material to irradiation light is important in the present method.

Figure 8:
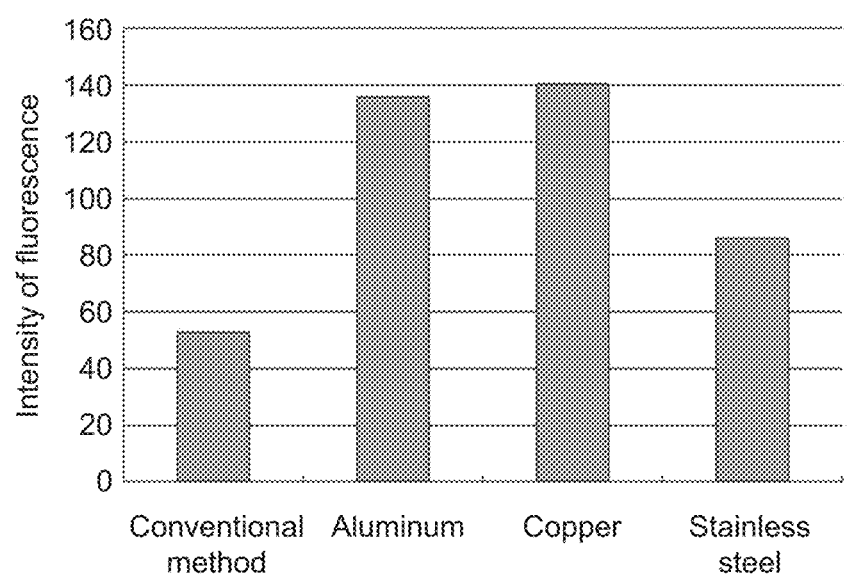
FIG. 8 is a graph showing an effect of reflection when various kinds of metal foils are used as a light-reflecting material.

In the present Example, the light having a wavelength of 365 nm was used as the irradiation light, however the wavelength of the irradiation light is not limited to 365 nm. When the light having a wavelength of 600 nm is used as the irradiation light, copper as equally as aluminum efficiently reflects the light with a reflectance of about 90% and it can be said that copper is effective as a light-reflecting material to the irradiation light having a wavelength of 600 nm. When particles that emit fluorescence at 600 nm by being excited at 570 nm was used and irradiated with the irradiation light having a wavelength of 490 nm and fluorescence at 615 nm was detected, the detection light was amplified by copper as equally as aluminum (FIG. 8).

It is important to select a raw material that efficiently reflects the wavelength of irradiation light regardless of the wavelength of irradiation light to be used.

Example 3 Amplification of Detection Light with Light-Reflecting Material Provided at Lower Portion of Immunochromatographic Test Piece when Colored Polystyrene Particles are Used 1. Mouse IgG purified by affinity chromatography using a protein A column was diluted with purified water so as to be 1.0 mg/mL, red colored polystyrene particles were added thereto so as to be 0.1% to stir, then carbodiimide was added so as to be 1%, and the resultant mixture was further stirred. The supernatant was removed by a centrifugal operation, and the rest of the mixture was resuspended in 50 mM Tris (pH of 9.0) and 3% BSA to obtain mouse-derived antibody-labeled colored polystyrene particles.
2. Immobilization of Anti-Mouse IgG Antibody to Nitrocellulose Membrane A liquid obtained by diluting anti-mouse IgG antibody with purified water so as to be 1.0 mg/mL was applied in a line shape at a predetermined portion of a nitrocellulose membrane lined with a PET film, and dried at 45° C. for 30 minutes to obtain an antibody-immobilized membrane (hereinafter, denoted as antibody-immobilized membrane).
3. Accumulation of Colored Polystyrene Particles at Immobilized Portion by Immunochromatography The antibody-immobilized membrane obtained in 2, a backing sheet, an absorption band, a conjugate pad, and a sample pad were stuck together to make a test piece, and the test piece not containing a light-reflecting material was denoted as a conventional test piece (FIG. 4A). Moreover, the members were stuck together to make a test peace holding a light-reflecting material under the antibody-immobilized membrane and on the backing sheet, and the test piece including the light-reflecting material was denoted as a test piece of the method according to the present invention (FIG. 4B).

On the sample pad of the test piece, 50 μl of a specimen-suspended liquid (10 mM Tris (pH of 7.0), 3% BSA, and 0.2% Triton X-100) was dropped. After the resultant mixture was left standing at 15 minutes, the antibody-immobilized portion and the portion surrounding the antibody-immobilized portion on the test piece were irradiated with irradiation light (green LED) with a reader dedicated to immunochromatography, and the intensity of detection light reflected by the test piece and the colored polystyrene particles was measured.

Figure 9A:
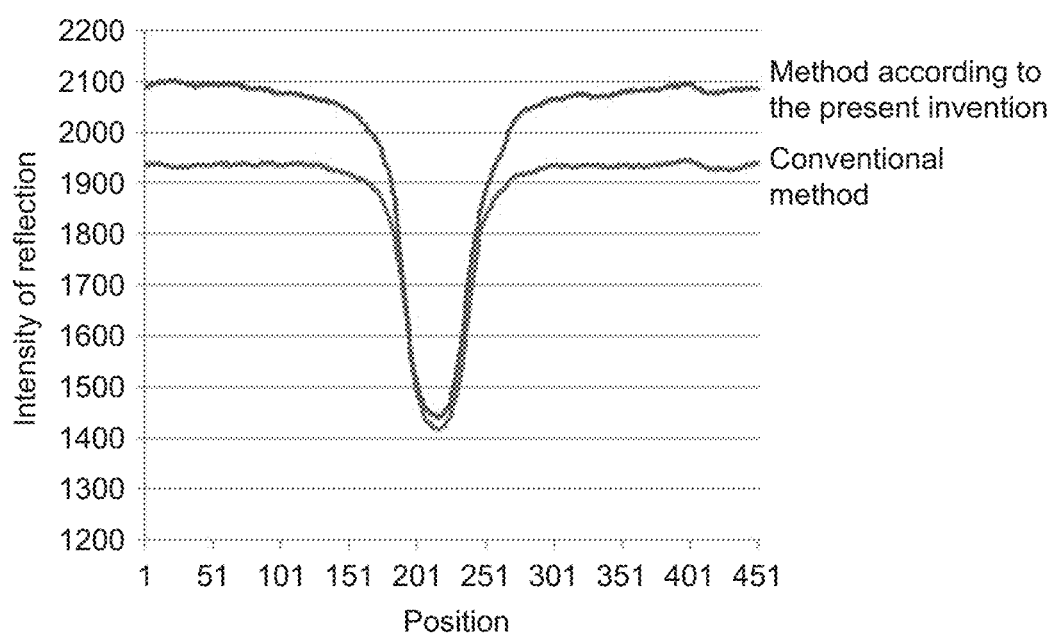
FIG. 9A is a graph showing an effect of reflection using a light-reflecting material when colored polystyrene particles are used.
Figure 9B:
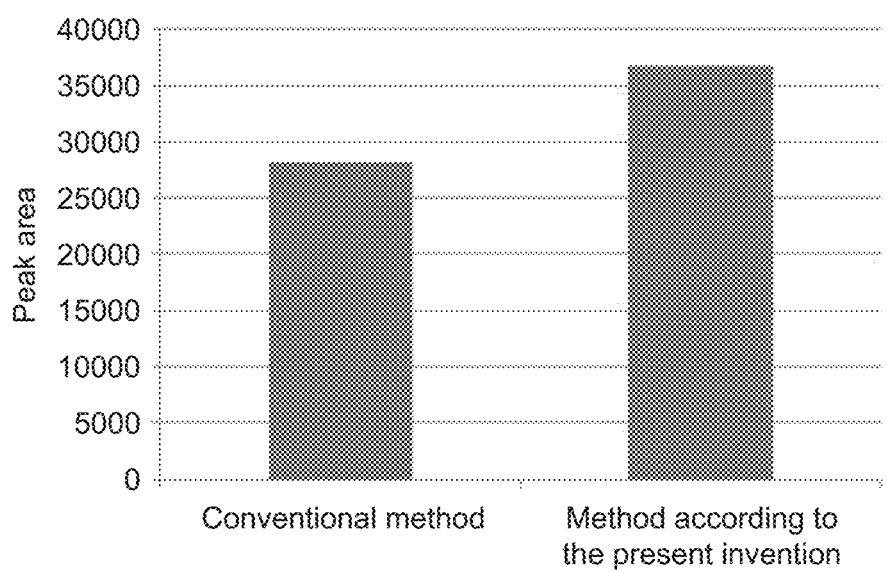
FIG. 9B is a graph showing attenuation of reflected light of irradiation light due to particles when colored polystyrene particles are used.

FIG. 9A shows the relationship of the position on an immunochromatographic test piece and the intensity of reflected light at the position. FIG. 9A shows the result of the conventional test piece and the result of the test piece of the method according to the present invention. The center portion where the intensity of reflected light is low (near the positions 201 to 251) shows a portion where the colored polystyrene particles are accumulated. Moreover, FIG. 9B is a graph showing a peak area at the portion where the reflected light is attenuated due to an influence of the colored polystyrene particles and the intensity of reflected light is lowered in FIG. 9A. As shown in FIG. 9A, the intensity of reflected light emitted at the portion surrounding and other than the portion where the colored polystyrene particles are accumulated was clearly amplified when the method according to the present invention was used when compared with the case where the conventional test piece was used. Moreover, as shown in FIG. 9B, the peak area at the portion where the reflected light is attenuated due to an influence of the colored polystyrene particles and the intensity of reflected light is lowered is larger in the method according to the present invention than in the conventional method. The results show that the attenuation of the reflected light of irradiation light is detected more clearly due to the colored polystyrene particles

REFERENCE SIGNS LIST a Absorption band
b Membrane
b' Detection portion
c Conjugated pad
d Sample pad
e Backing sheet
f Reflection material
g Backing sheet
h Cut portion All the publications, patents, and patent applications cited in the present description are taken in the present description as they are as reference.

The invention claimed is:
1. An immunochromatographic method for detecting a substance, the method comprising:
providing a device for detecting a substance in a liquid sample, the device comprising an immunochromatographic test piece and a storage container containing the test piece, the test piece comprising a membrane having thereon a detection portion and insoluble carrier particles bound to a ligand specific for the substance, wherein the detection portion comprises an immobilized ligand specific for the substance and the storage container comprises an inner surface, wherein a light reflecting material is attached to the inner surface at a position under the membrane and opposite to the side of the membrane comprising the detection portion, wherein the light reflecting material is metal and is shaped to provide a curved surface,
adding the liquid sample to the device so that the liquid sample contacts the membrane, wherein the sample flows through the membrane and contacts the insoluble carrier particles to form a complex between the insoluble carrier particles and the substance,
accumulating the complex between the insoluble carrier particles and the substance at the detection portion by capturing the complex at the detection portion by the detection portion immobilized ligand specific for the substance,
irradiating the membrane at the detection portion with excitation light, wherein the excitation light penetrates the membrane at the detection portion and is reflected by the curved surface of the light reflecting material and focused back onto the detection portion to cause the insoluble carrier particles to emit amplified light, detecting the amplified light emitted by the insoluble carrier particles at the detection portion where the insoluble carrier particles accumulated or at a portion of the membrane adjacent to the detection portion where the insoluble carrier particles accumulated, thereby detecting the substance.

2. The method according to claim 1, wherein the insoluble carrier particles are fluorescent labeled insoluble carrier particles.

3. The method according to claim 1, wherein the insoluble carrier particles are colored polystyrene insoluble carrier particles.

4. The method according to claim 1, wherein the metal is selected from the group consisting of aluminum and copper.

5. The method according to claim 4, wherein the membrane is irradiated with excitation light having a wavelength of 250 nm to 1000 nm when the metal is aluminum, and the membrane is irradiated with excitation light having a wavelength from 600 nm to 1000 nm when the metal is copper.

6. The method according to claim 1, wherein the substance to be detected is an antigen or is an antibody.

* * * * *